(12) United States Patent
Hansmann

(10) Patent No.: US 11,739,745 B2
(45) Date of Patent: Aug. 29, 2023

(54) COMPRESSIBLE FLUID MICROPUMP SYSTEM AND PROCESS

(71) Applicant: Drägerwerk AG & Co. KGaA, Lübeck (DE)

(72) Inventor: Hans-Ullrich Hansmann, Barnitz (DE)

(73) Assignee: Drägerwerk AG & Co KGaA, Lübeck (DE)

( * ) Notice: Subject to any disclaimer, the term of this patent is extended or adjusted under 35 U.S.C. 154(b) by 222 days.

(21) Appl. No.: 16/912,277

(22) Filed: Jun. 25, 2020

(65) Prior Publication Data

US 2020/0408202 A1 Dec. 31, 2020

(30) Foreign Application Priority Data

Jun. 26, 2019 (DE) ...................... 10 2019 004 450.9

(51) Int. Cl.
*F04B 43/04* (2006.01)
*H05K 1/18* (2006.01)
(Continued)

(52) U.S. Cl.
CPC ............ *F04B 43/046* (2013.01); *F04B 41/06* (2013.01); *F04B 49/06* (2013.01); *H05K 1/145* (2013.01);
(Continued)

(58) Field of Classification Search
USPC .......................... 361/688, 694, 695; 165/905
See application file for complete search history.

(56) References Cited

U.S. PATENT DOCUMENTS

| | | | | |
|---|---|---|---|---|
| 4,808,084 A | * | 2/1989 | Tsubouchi | F04B 43/04 417/322 |
| 4,938,742 A | * | 7/1990 | Smits | F04B 43/046 222/255 |

(Continued)

FOREIGN PATENT DOCUMENTS

| | | |
|---|---|---|
| CA | 2350076 A1 | 5/2000 |
| CN | 2233069 Y * | 8/1996 |

(Continued)

OTHER PUBLICATIONS

Machine Translation of CN-2233069 (Obtained from USPTO Search, copyright 2022, Clarivate Analytics) copy is attached to the Foreign Patent Document (Year: 2022).*

(Continued)

*Primary Examiner* — Essama Omgba
*Assistant Examiner* — Geoffrey S Lee
(74) *Attorney, Agent, or Firm* — McGlew and Tuttle, P.C.

(57) ABSTRACT

A micropump system (100) for a compressible fluid (102) includes a plurality of micropumps (110), rigid flow duct elements (120), a control unit (130), and one or two printed circuit boards (140). The micropumps have an intake opening (112) and an outlet opening (114). The rigid flow duct elements are connected to a respective micropump via a respective, elastically sealed port (122) and with the micropumps form a flow path (104) for the fluid. The one or two printed circuit boards are arranged and configured to electrically connect the control unit to the plurality of micropumps. Each micropump is rigidly fastened to the one or two printed circuit boards via a respective fastening device. A pressure build-up of the fluid flowing through the plurality of micropumps during the use, which is cascaded due to the plurality of micropumps, is provided at a system outlet (106) of the micropump system.

20 Claims, 7 Drawing Sheets

(51) Int. Cl.
  *H05K 1/14*   (2006.01)
  *F04B 49/06*  (2006.01)
  *F04B 41/06*  (2006.01)
  *H05K 7/20*   (2006.01)

(52) U.S. Cl.
  CPC ......... *H05K 1/181* (2013.01); *H05K 7/20136* (2013.01); *H05K 2201/042* (2013.01)

(56) References Cited

U.S. PATENT DOCUMENTS

| | | | | |
|---|---|---|---|---|
| 5,001,548 | A * | 3/1991 | Iversen | H01L 23/473 |
| | | | | 257/E23.098 |
| 5,078,581 | A * | 1/1992 | Blum | F04B 45/047 |
| | | | | 417/413.3 |
| 5,215,446 | A * | 6/1993 | Takahashi | F04B 43/046 |
| | | | | 417/322 |
| 5,566,377 | A * | 10/1996 | Lee | G06F 1/20 |
| | | | | 361/695 |
| 5,836,750 | A * | 11/1998 | Cabuz | F04B 43/14 |
| | | | | 417/322 |
| 6,827,559 | B2 * | 12/2004 | Peters | F04B 43/046 |
| | | | | 417/248 |
| 6,919,669 | B2 * | 7/2005 | Bryant | H04R 17/00 |
| | | | | 310/365 |
| 7,163,385 | B2 * | 1/2007 | Gharib | F04B 43/08 |
| | | | | 417/474 |
| 7,380,916 | B2 * | 6/2008 | Sugahara | B41J 2/14233 |
| | | | | 347/68 |
| 7,397,164 | B1 * | 7/2008 | Ali | G06F 1/203 |
| | | | | 310/311 |
| 7,397,166 | B1 * | 7/2008 | Morgan | F04B 43/1223 |
| | | | | 417/322 |
| 8,678,787 | B2 | 3/2014 | Hirata et al. | |
| 8,979,510 | B2 * | 3/2015 | Shin | F04B 43/14 |
| | | | | 417/413.1 |
| 2002/0039280 | A1 * | 4/2002 | O'Connor | H01L 23/473 |
| 2002/0124896 | A1 | 9/2002 | O'Connor et al. | |
| 2002/0184907 | A1 * | 12/2002 | Vaiyapuri | H01L 23/473 |
| | | | | 361/689 |
| 2009/0060762 | A1 * | 3/2009 | Ishikawa | F04B 43/046 |
| | | | | 310/317 |
| 2011/0005606 | A1 * | 1/2011 | Bartels | F04B 43/095 |
| | | | | 137/565.01 |
| 2015/0025461 | A1 | 1/2015 | Corso et al. | |
| 2015/0260181 | A1 | 9/2015 | Harvey | |
| 2016/0103104 | A1 | 4/2016 | Gianchandani et al. | |
| 2018/0117243 | A1 * | 5/2018 | Maguire | A61M 5/14228 |
| 2021/0252757 | A1 * | 8/2021 | Prystupa | B01L 3/502792 |
| 2021/0404460 | A1 * | 12/2021 | Ikeda | B65D 83/00 |

FOREIGN PATENT DOCUMENTS

| | | |
|---|---|---|
| CN | 2821218 Y | 9/2006 |
| DE | 10154822 A1 | 5/2003 |
| DE | 102004062923 A1 | 7/2006 |
| DE | 102018120782 B3 | 8/2019 |
| TW | 200713410 A | 4/2007 |

OTHER PUBLICATIONS

Bartels Mikrotechnik Product Guide (Jan. 2012) (Year: 2012).*

* cited by examiner

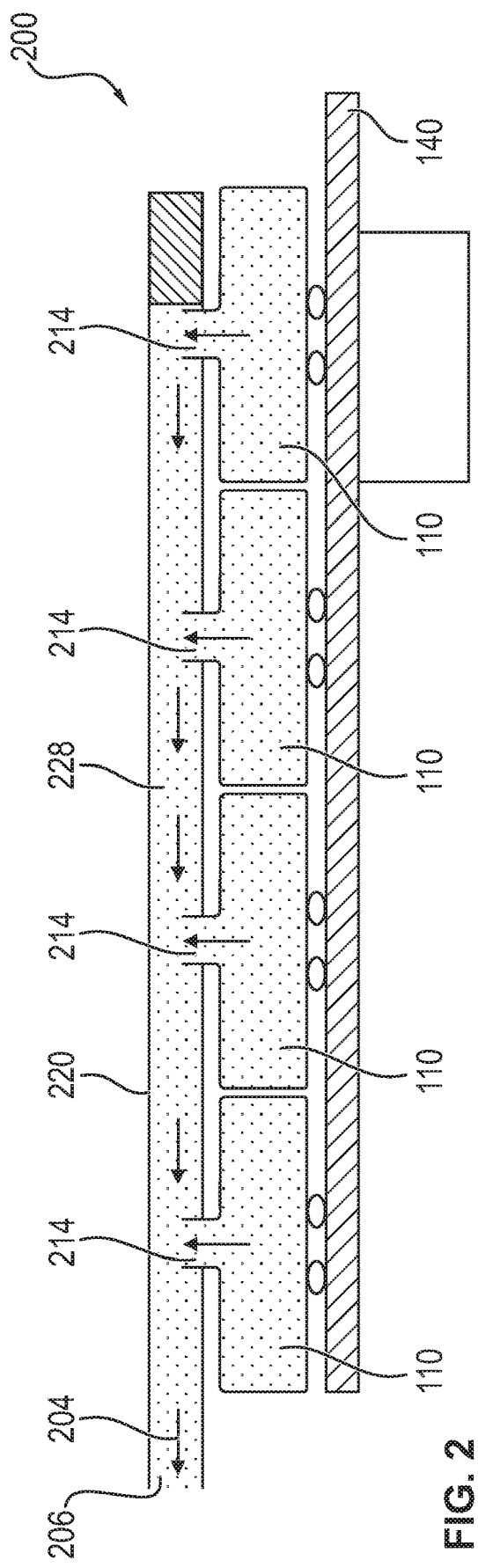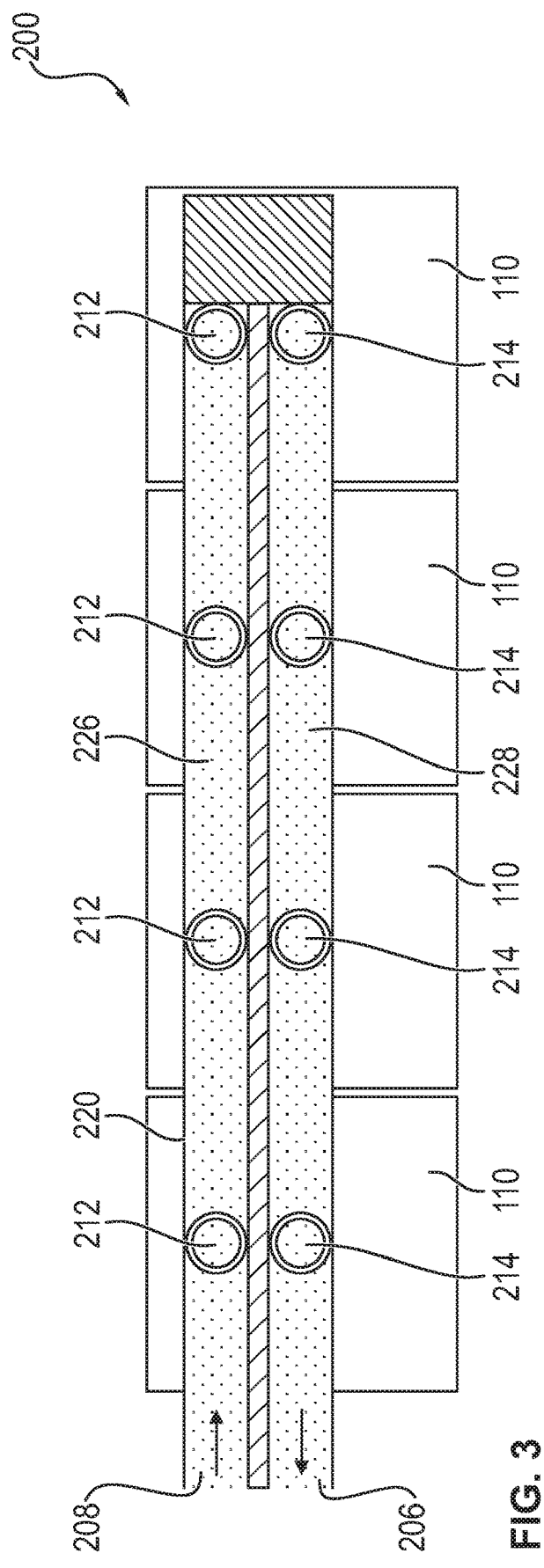
FIG. 2
FIG. 3

COMPRESSIBLE FLUID MICROPUMP SYSTEM AND PROCESS

CROSS REFERENCE TO RELATED APPLICATIONS

This application claims the benefit of priority under 35 U.S.C. § 119 of German Application 10 2019 004 450.9, filed Jun. 26, 2019, the entire contents of which are incorporated herein by reference.

TECHNICAL FIELD

The present invention pertains to a micropump system for the transport of a compressible fluid and to a process for transporting a compressible fluid.

TECHNICAL BACKGROUND

The use of micropumps for liquids or compressible fluids, for example, gases is known in various technical fields. Micropumps are thus used, for example, to cool electronic components.

U.S. Pat. No. 8,678,787 B2 describes a micropump, which has an inertia swing unit operated via a piezoelectric element. In this case, a repeated changing of the expansion of the piezoelectric element leads to a diaphragm of the inertia swing unit moving at a predefined frequency and a flow direction of a gas to be carried being adjusted due to the described architecture of the micropump. Such micropumps are typically operated in the high-frequency range.

SUMMARY

An object of the present invention is to make possible an improved micropump system, especially a micropump system, which can be provided in an especially simple manner and which is especially reliable.

A micropump system for the transport of a compressible fluid with a plurality of micropumps, with a number of rigid flow duct elements, with a control unit and with one or two printed circuit boards is provided according to the present invention to accomplish this object.

The micropumps comprising the plurality of micropumps have each an intake opening and an outlet opening for the fluid and are each configured to draw in the fluid through the intake opening, which fluid flows through the micropump system during the use thereof, due to an electrically controlled inertia swing unit of the respective micropump and to discharge same through the outlet opening.

The flow duct elements comprising the number of rigid flow duct elements are connected to the intake opening or to the outlet opening of a respective micropump via a respective, elastically sealed port and form together with the plurality of micropumps a flow path for the fluid.

The control unit is configured to control the operation of the plurality of micropumps. The control unit comprises one or more processors.

The one or two printed circuit boards are arranged and configured to electrically connect the control unit to the plurality of micropumps, wherein each micropump comprising the plurality of micropumps is rigidly fastened to the one or two printed circuit boards via a respective fastening device, and wherein a pressure build-up of the fluid flowing through the plurality of micropumps during the use, which pressure build-up is cascaded due to the plurality of micropumps, is provided at a system outlet of the micropump system.

It was found within the scope of the present invention that an especially simple assembly of a plurality of micropumps is possible due to a correspondingly provided assembly plane on the one or two printed circuit boards. Further, it was found that the rigid fastening of the micropump via the respective fastening device and the rigid connection of the micropumps to one another via the rigid flow duct elements may contribute to the avoidance of dead spaces within the micropump system.

Due to the avoidance of dead spaces according to the present invention, the response time at the start of the operation of the micropump system can be reduced and the efficiency of the micropump system can be improved. Thus, due to the micropump system according to the present invention, using the pump output for the deformation of elastic connection elements instead of using them for the desired transport of the compressible fluid is avoided.

The compact construction of the micropump system proposed within the scope of the present invention additionally contributes to the avoidance of dead spaces. Further, the proposed compact construction makes possible the use of a small number and a small size of rigid flow duct elements. Finally, the proposed structure consisting of a printed circuit board or printed circuit boards with the rigidly connected micropumps allows an especially small size of the micropump system.

Furthermore, the use of single rigid flow duct elements that have a hollow configuration according to the present invention in order to thereby form the flow path allows the simple replacement of a single flow duct element for the cleaning or repair of this flow duct element. A respective flow duct element typically has an elongated configuration and has a cavity enclosed by a respective rigid wall, the openings of which are formed by at least two connection areas for the elastically sealed port to a respective opening of a micropump.

Furthermore, the proposed rigid fastenings and the rigid connections of the micropumps to one another lead to a low vibration of a respective micropump within the micropump system. As a result, the proposed micropump system is especially reliable and quiet for micropumps operated at a high frequency.

The cascaded pressure build-up provided, by means of which it is possible to provide an especially high overall pump pressure of the micropump system, is especially advantageous of the micropump system according to the present invention. Consequently, the micropump system is suitable for especially many applications, for which now a plurality of micropumps with low pump pressure can be used instead of a single pump with high pump pressure.

A preferred application of the proposed micropump system is in the medical field. Thus, a patient gas can be carried in an especially efficient manner to a patient to be supplied therewith by means of the compact micropump system provided. DE 10 2018 120 782 B3 provides a further example of a micropump comprising an inertia swing unit (momentum unit having a piezo actuator) that may be used according to the micropump system and process of the invention. DE 10 2018 120 782 B3 and U.S. Pat. No. 8,678,787 are incorporated herein by reference.

The proposed structured configuration of the micropump system according to the present invention advantageously makes possible an automated production, as a result of which low production costs are made possible. In particular, this structured configuration makes it possible that micropump systems for various applications can be assembled with different additional system elements each with the same structure. Thus, the use of the same printed circuit board or the same printed circuit boards for different micropump systems and especially for different applications is advantageously possible as well depending on the additional system elements.

The flow path for the fluid leads through at least one micropump, through which the fluid flows, and through at least one rigid flow duct element, which is connected to this micropump via the elastically sealed port.

According to the present invention, the number of rigid flow duct elements may consist of a single flow duct element.

The plurality of micropumps comprise at least two micropumps, preferably at least four micropumps.

The control unit may be arranged fixed to the one or two printed circuit boards. In an alternative embodiment, the control unit is configured at a spaced location from the printed circuit board.

The cascaded pressure build-up is provided according to the present invention by at least two micropumps comprising the plurality of micropumps having discharged the fluid provided, especially the gas provided at the system outlet. This object can be carried out, for example, by a connection in series or parallel connection of the at least two micropumps within the micropump system, as this is described in detail within the scope of the description of the figures.

The basic configuration of the micropumps, as they can be used within the scope of the micropump system according to the present invention, is known to the person skilled in the art and will hence not be described in detail below. A general structure of such a configuration is explained within the scope of FIG. 6.

Preferred embodiments of the micropump system according to the present invention are described below.

In an especially advantageous embodiment, at least one rigid flow duct element rigidly connects the respective outlet opening of a micropump, which is arranged upstream in relation to the direction of flow of the fluid flowing through, to the respective intake opening of a micropump, which is arranged downstream in relation to this direction of flow, to one another. Such a rigid connection advantageously leads to a connection in series of two micropumps. Due to the connection in series of two micropumps, a doubled pump pressure can be provided compared to a single micropump. In this embodiment, the compact connection of a plurality of micropumps within the micropump system is thus advantageously used to provide an elevated pump pressure at the system outlet.

In a variant of the previous embodiment, all micropumps comprising the plurality of micropumps are connected to one another by the rigid flow duct elements due to the corresponding connection of an outlet opening of a respective upstream micropump to an intake opening of a respective downstream micropump. In this variant, the micropump system according to the present invention consists of a single connection in series of the provided micropumps comprising the plurality of micropumps. As a result, the plurality of micropumps are used especially efficiently to provide a high overall pump pressure. In this case, a number of N micropumps lead to an N-fold pump pressure compared to a single micropump.

In another advantageous embodiment, the number of flow duct elements are configured and arranged such that they form a feed line, which is rigidly connected to all intake openings of the plurality of micropumps, and a discharge line, which is rigidly connected to all outlet openings of the plurality of micropumps. In this embodiment, all micropumps are connected parallel to one another. As a result, the simple pump pressure of a single micropump, but an increased flow corresponding to the plurality of micropumps, is provided at the system outlet of the micropump system. In this case, a number of N micropumps connected in parallel lead to an N-fold flow of the fluid flowing through the micropump system compared to a single micropump. As a result, especially large quantities of the compressible fluid can consequently be moved via the micropump system.

In another embodiment, the micropump system consists both of micropumps connected in series to one another and of micropumps connected parallel to one another from the plurality of micropumps. This is especially advantageous in order to provide an increased flow of the fluid compared to a single micropump and at the same time an increased overall pump pressure compared to a single micropump.

The compressible fluid is preferably a gas.

In an especially preferred embodiment, the respective, elastically sealed port is elastically sealed via an O-ring. The sealing of the sealed port can be provided in an especially cost-effective manner as a result. Furthermore, using an O-ring leads to a uniform thermal expansion in case of a heating up of the micropump system according to the present invention. As a result, one-sided loading of the sealing is avoided and a reliable operation of the micropump system at elevated temperatures is also made possible.

The fastening device for the rigid fastening of a respective micropump to a printed circuit board is formed by a soldering pad, a soldering pin or a rigid plug-type (plug) connection in another preferred embodiment. In this embodiment, the fastening device can be manufactured in an especially cost-effective manner. Furthermore, the use of a soldering pad and/or soldering pin allows an especially simple and reliable fastening of a respective micropump to a printed circuit board. Furthermore, such a fastening can be provided in an especially simple manner within the scope of an automated process.

In another advantageous embodiment, a nonreturn valve is arranged at the system outlet of the micropump system for ensuring a minimum pressure provided by the micropump system. In an advantageous variant, the nonreturn valve is likewise rigidly fastened to a printed circuit board of the micropump system. A rigid flow duct element comprising the number of rigid flow duct elements carries the fluid from at least one micropump comprising the plurality of micropumps to the nonreturn valve. Ensuring the minimum pressure allows a fast detection of an error within the micropump system, for example, of a failure of a micropump.

In an embodiment in addition to or as an alternative to the previous embodiment, a pressure sensor is arranged at the system outlet of the micropump system to ensure a minimum pressure provided by the micropump system. In an advantageous variant, the pressure sensor is also rigidly fastened to a printed circuit board of the micropump system. A rigid flow duct element comprising the number of rigid flow duct elements advantageously carries the fluid from at least one micropump comprising the plurality of micropumps to the pressure sensor.

In an especially preferred embodiment, the micropump system according to the present invention has a printed circuit board, which is a flat printed circuit board and on which the plurality of micropumps are fastened with the respective rigid fastening device such that all micropumps are arranged in a common fastening plane on the printed circuit board, and wherein the fastening plane is parallel to the plane formed by the printed circuit board. Such a division of the fastening plane and the printed circuit board leads to an especially structured arrangement of the micropump system and thereby reduces error sources during the assembly and operation of this micropump system. Furthermore, this structure allows an especially simple automated production of the micropump system according to the present invention.

In another preferred embodiment, the number of flow duct elements are connected to the micropumps such that they form a common connection plane. An especially simple structure of the micropump system according to the present invention is ensured as a result. Due to ensured accessibility to the connection plane, the assembly of the flow duct elements can be especially simple. Furthermore, error sources during the assembly and operation of this micropump system are reduced due to this structure arrangement. Moreover, this structure allows an especially simple automated production of the micropump system according to the present invention.

In an especially advantageous variant of the two previous embodiments, the connection plane is, furthermore, parallel to the plane formed by the printed circuit board. This leads to an additional simplification of the structure of the micropump system. Such a construction with a plurality of elements arranged parallel to one another may, furthermore, contribute to the micropump system having an especially compact configuration.

In an advantageous embodiment, the respective electrical connection between the printed circuit board and the micropump is formed by a soldered joint, an electrical cable and/or by a plug-type connection. These electrical connections may be provided in an especially cost-effective manner. Furthermore, these electrical connections allow the manufacture of the micropump system by means of a simple process that can be automated.

In another embodiment, the micropump system comprises two printed circuit boards which are aligned parallel to one another. In this case, the micropumps comprising the plurality of micropumps are each fastened to one of the two opposite sides between the two printed circuit boards. The parallel alignment of the two printed circuit boards advantageously allows an especially compact construction of the micropump system. The fastening of the micropump on the opposite sides of the printed circuit boards advantageously makes possible the connection of micropumps of different printed circuit boards by means of a short flow duct element.

In another embodiment, the micropump system additionally has at least one additional system element, for example, a filter, a flow resistor or a cavity.

A compact construction of the micropump system according to the present invention preferably makes possible the use of short rigid flow duct elements, due to which dead spaces are, moreover, avoided and which reduce the elasticity of the entire system or of parts of the system.

According to a preferred aspect of the present invention, the micropump system according to the present invention is used within a medical system, especially within a medical ventilation system.

According to another aspect of the present invention, a process for transporting a compressible fluid is provided for accomplishing the above-mentioned object. According to the present invention, this process has the following steps:

provision of a plurality of micropumps, which have each an intake opening and an outlet opening for the fluid and which are each configured to draw in the fluid through the intake opening, which fluid flows through a correspondingly formed micropump system during the use thereof, due to an electrically controlled inertia swing unit of the respective micropump and to discharge same through the outlet opening, formation of a flow path for the fluid due to a connection of a number of rigid flow duct elements to a respective micropump via a respective, elastically sealed port, and electrical connection of one or two printed circuit boards to the plurality of micropumps and rigid fastening of each micropump from the plurality of micropumps via a respective fastening device to the one or two printed circuit boards, wherein a pressure build-up of the fluid flowing through the plurality of micropumps during the use, which pressure build-up is cascaded due to plurality of micropumps, is provided at a system outlet of the micropump system.

The transport of the fluid according to this process advantageously allows the avoidance of dead spaces within the flow path.

Furthermore, the rigid flow duct elements and the rigid fastening between the micropump and the printed circuit board lead to a low elasticity and to a low susceptibility of the provided transport to vibrations, as are usually present during the operation of a micropump.

Finally, the cascaded pressure build-up allows a high overall pump pressure in the flow path provided according to the present invention. This allows a wide range of possible applications of the process according to the present invention, since such a provided flow path may have very different dimensions in regard to the transported fluid volume and of the overall pump pressure provided.

The process according to the present invention is preferably used within a medical system, especially within a medical ventilation system.

The present invention shall now be explained in more detail on the basis of advantageous exemplary embodiments, which are schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic side view of a second exemplary embodiment of a micropump system according to the present invention, in which individual micropumps are connected in parallel;

FIG. 3 is a schematic top view of a second exemplary embodiment of a micropump system according to the present invention, in which individual micropumps are connected in parallel;

DESCRIPTION OF PREFERRED EMBODIMENTS

Figure 1:
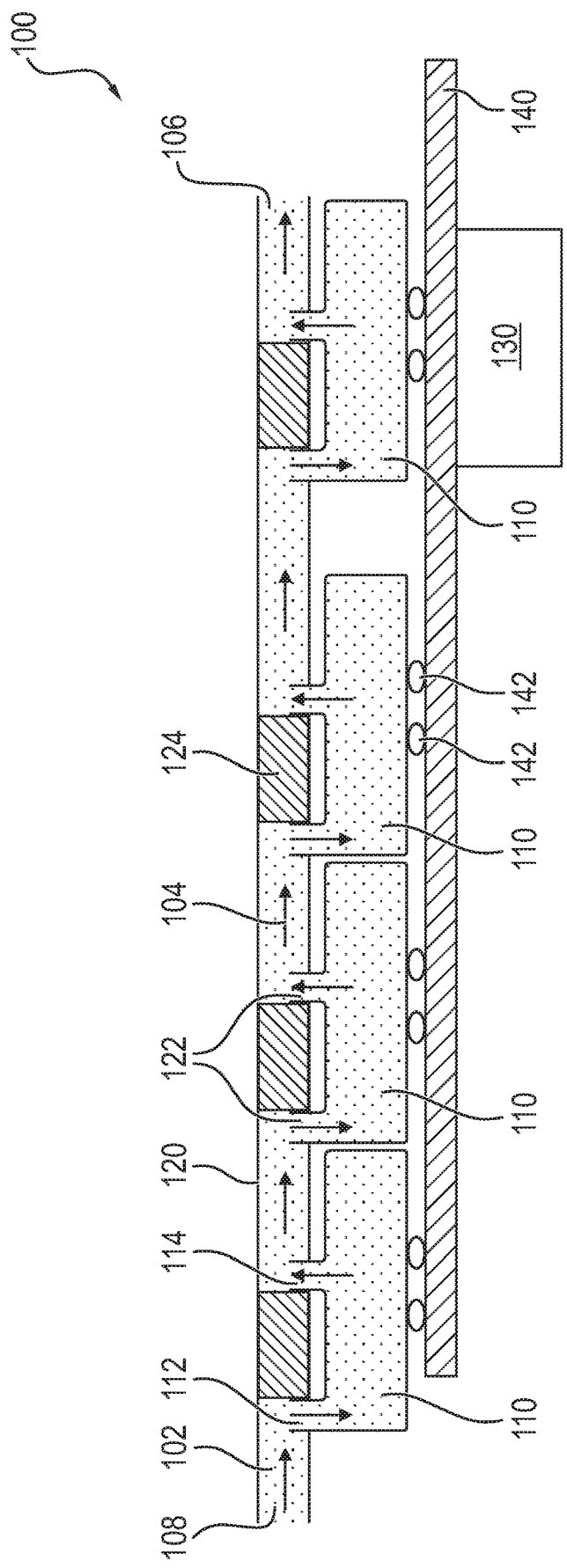
FIG. 1 is a schematic view of a first exemplary embodiment of a micropump system according to the present invention, in which individual micropumps are connected in series.

Referring to the drawings, FIG. 1 shows a schematic view of a first exemplary embodiment of a micropump system 100 according to the present invention, in which individual micropumps 100 are connected in series.

The micropump system 100 shown for the transport of a compressible fluid 102, especially of a gas, has a plurality of micropumps 110, a number of rigid flow duct elements 120, a control unit 130 and a printed circuit board 140.

The micropumps 110 comprising the plurality of micropumps 110 have each an intake opening 112 and an outlet opening 114 for the fluid 102 and are each configured to draw in the fluid 102 through the intake opening 112, which fluid flows through the micropump system 100 during the use thereof, due to an electrically controlled inertia swing unit 115 (described in FIG. 6) of the respective micropump 110 and to discharge same through the outlet opening 114. In this connection, the architecture of the respective micropump 110 ensures that a flow direction with a corresponding flow path 104 is predefined. In an exemplary embodiment, not shown, a nonreturn valve within the respective micropump ensures that the flow direction of the fluid flowing through the micropump is predefined.

In the exemplary embodiment shown, the number of micropumps 110 comprise precisely four micropumps 110, which all have a configuration of identical design.

The number of rigid flow duct elements 120 have each two ports 122, which are configured such that they are connected to a respective micropump 110 in an elastically sealed manner. In the exemplary embodiment shown, a respective, elastically sealed port 122 is provided via a respective O-ring. In an example, not shown, a material for sealing is applied to the edge of a respective port. Together with the plurality of micropumps 110, the rigid flow duct elements 120 form the flow path 104 for the fluid 102. The number of flow duct elements 120 are formed in the exemplary embodiment shown by a single flow duct element, which is attached to all pumps, and have a respective blocking element 124 in the area of a respective micropump 110 such that the fluid is carried through the corresponding micropump 110. Further, in the exemplary embodiment shown, three of the four micropumps 110 are aligned equidistantly to one another and only one micropump 110 in the area of a system outlet 106 of the micropump system 100 is configured as arranged at a spaced location from the other micropumps 110.

The control unit 130 is arranged on the side of the printed circuit board 140 located opposite to the micropump 110 and is configured to control the operation of the plurality of micropumps.

The printed circuit board 140 is arranged and configured to electrically connect the control unit 130 to the plurality of micropumps 110. In the exemplary embodiment shown, the electrical connection is carried out by a respective soldered joint 142, especially a soldering pin and/or a soldering pad, via which each of the micropumps 110 is rigidly connected to the printed circuit board 140. The printed circuit board 140 is a printed circuit board in the exemplary embodiment shown.

The shown structure of the micropumps 110 on the printed circuit board 140 with the correspondingly provided flow path 104 leads to a cascaded pressure build-up of the fluid 102 flowing through the plurality of micropumps 110 during the use at the system outlet 106 of the micropump system 100. In view of the flow path 104, the four micropumps 110 are connected in series to one another, so that an overall pump pressure, which corresponds to the fourfold pump pressure of a single micropump 110, is provided at the system outlet 106.

The system outlet 106 is arranged in relation to a system inlet 108 on the printed circuit board 140 on an opposite side of the micropump system 100.

The micropump system 100 shown is suitable for applications, in which a higher pump pressure is necessary than it could be provided by a single micropump. In particular, the micropump system 100 shown is intended for a medical application, preferably a medical application within a ventilator.

FIGS. 2 and 3 show a schematic view of a second exemplary embodiment of a micropump system 200 according to the present invention, in which individual micropumps 110 are connected in parallel, in a side view (FIG. 2) and in a top view (FIG. 3).

Compared to the micropump system 100 shown in FIG. 1, both the intake openings 212 of the four micropumps 210 of identical design shown are arranged slightly offset and the rigid flow duct element 220 has a different configuration from the flow duct element 120.

The flow duct element 220 has a feed line 226, which is rigidly connected to all intake openings 212 of the micropumps 210. Furthermore, the flow duct element 220 has a discharge line 228, which is connected to all outlet openings 214 of the plurality of micropumps 210. The feed line 226 and the discharge line 228 are parts of a single common flow duct element 220.

Due to the arrangement shown, the system outlet 206 is formed in the area of a system inlet 208.

The flow path 204 is divided into paths parallel to one another due to the arrangement shown. The fluid flowing through the flow path 204 is carried by a single micropump between the system inlet 208 and the system outlet 206. As a result, the arrangement shown therefore leads to a fourfold overall flow of the fluid flowing through at the system outlet 206 compared to a single micropump, with an overall pump pressure that corresponds to the pump pressure of a single micropump.

As already in the micropump system 100, the flow duct elements are also formed in the micropump system 200 such that a common connection plane is predefined by these flow duct elements. This connection plane is parallel to the printed circuit board 140.

Figure 4:
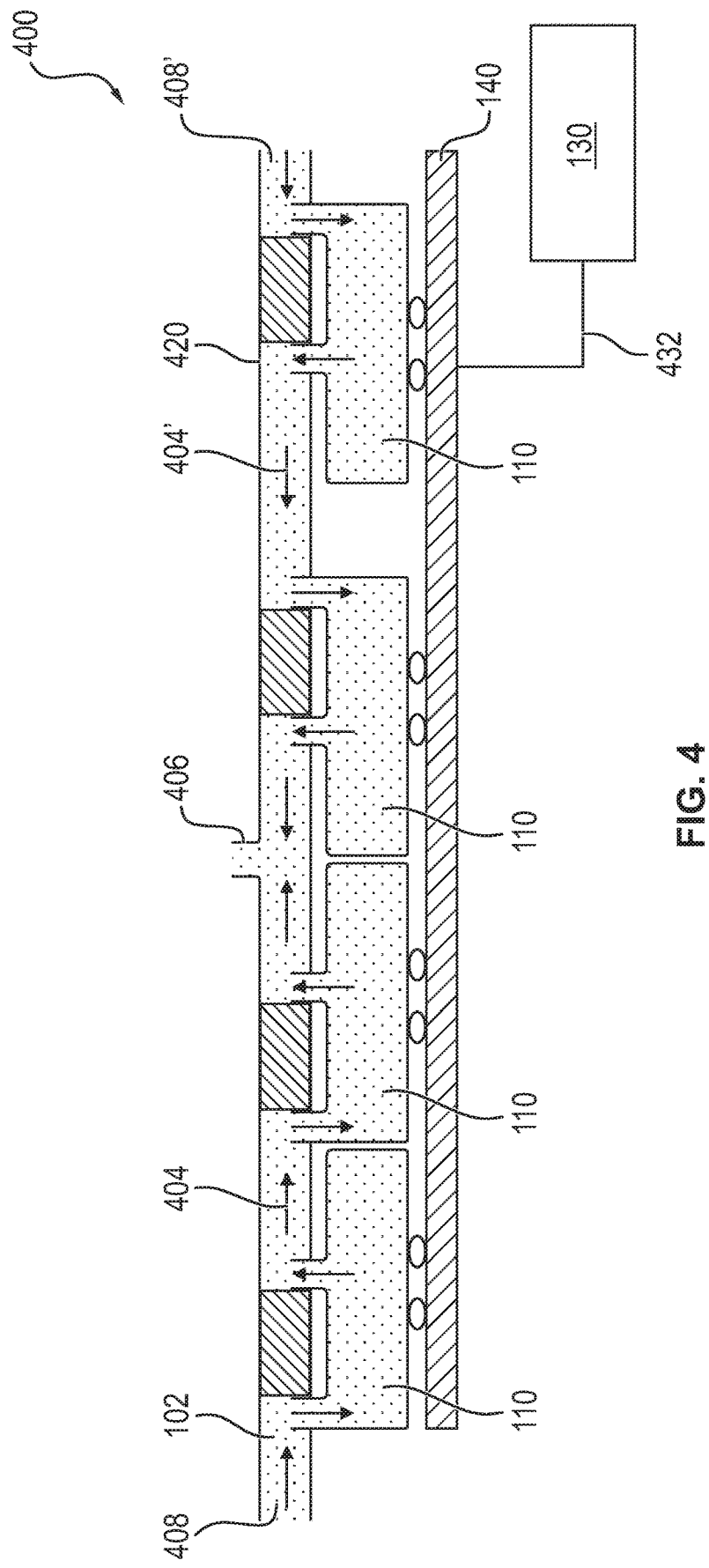
FIG. 4 is a schematic view of a third exemplary embodiment of a micropump system according to the present invention, in which individual micropumps connected in series are connected parallel to one another.

FIG. 4 shows a schematic view of a third exemplary embodiment of a micropump system 400 according to the present invention, in which individual micropumps 110 connected in series are connected parallel to one another.

As already in the two previous exemplary embodiments, the number of rigid flow duct elements are formed by a single flow duct element 420.

The micropump system 400 has two system inlets 408, 480', for two flow paths 404, 404' running parallel to one another, which are each formed from two micropumps 110 connected in series to one another. The two flow paths 404, 404' end at the common system outlet 406.

Consequently, an overall pump pressure, which is twice as high as the pump pressure of a single micropump 110, is applied to the system outlet 406. At the same time, the overall flow of the micropump system 400 shown is twice as great as the flow of the fluid 102 provided by a single micropump 110 due to the parallel transport of via the two flow paths 404, 404'.

The control unit 130 is arranged at a spaced location from the printed circuit board 140 and is connected to this printed circuit board via a cable 432. The control unit 130 activates the micropumps 110 via the cable 432 and the printed circuit board 140.

Figure 5:
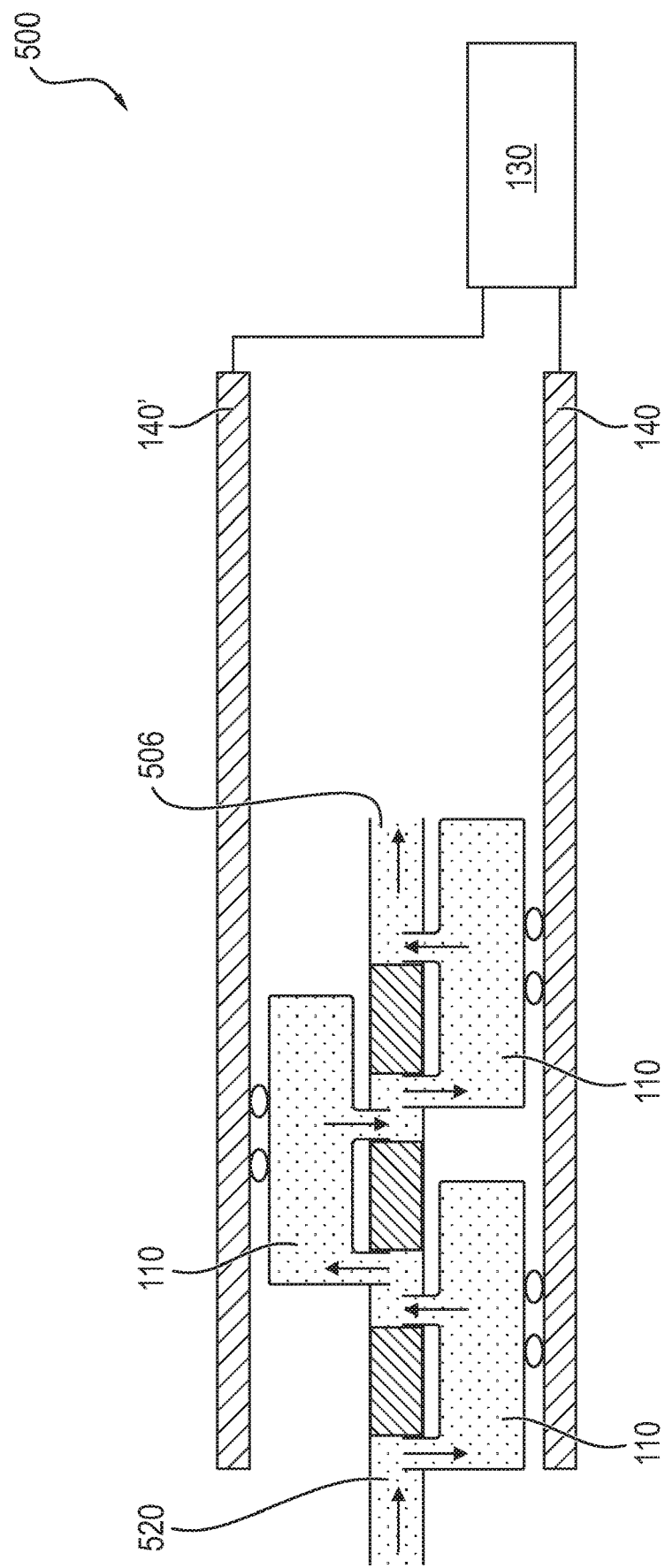
FIG. 5 is a schematic view of a fourth exemplary embodiment of a micropump system according to the present invention, in which micropumps are arranged on two printed circuit boards.

FIG. 5 shows a schematic view of a fourth exemplary embodiment of a micropump system 500 according to the present invention, in which micropumps 110 are arranged on two printed circuit boards 140, 140'.

The two flat printed circuit boards 140, 140' are aligned parallel to one another. The micropumps 110 that are arranged on the second printed circuit board 140' are located opposite the micropumps 110 that are arranged on the first printed circuit board 140, so that a connection can be provided via a rigid flow duct element 520. In the exemplary embodiment shown, both printed circuit boards are connected in a cable-based manner to the control unit 130.

The micropump system 500 comprises three micropumps 110, two of which are arranged on the first printed circuit board 140 and one of which is arranged on the second printed circuit board 140'. These three micropumps 110 are connected in series to one another, so that the threefold pump pressure of a single micropump is provided as the overall pump pressure at the system outlet 506.

The two printed circuit boards are preferably held in a predefined position in relation to one another via at least one spacer element (not shown).

Figure 6:
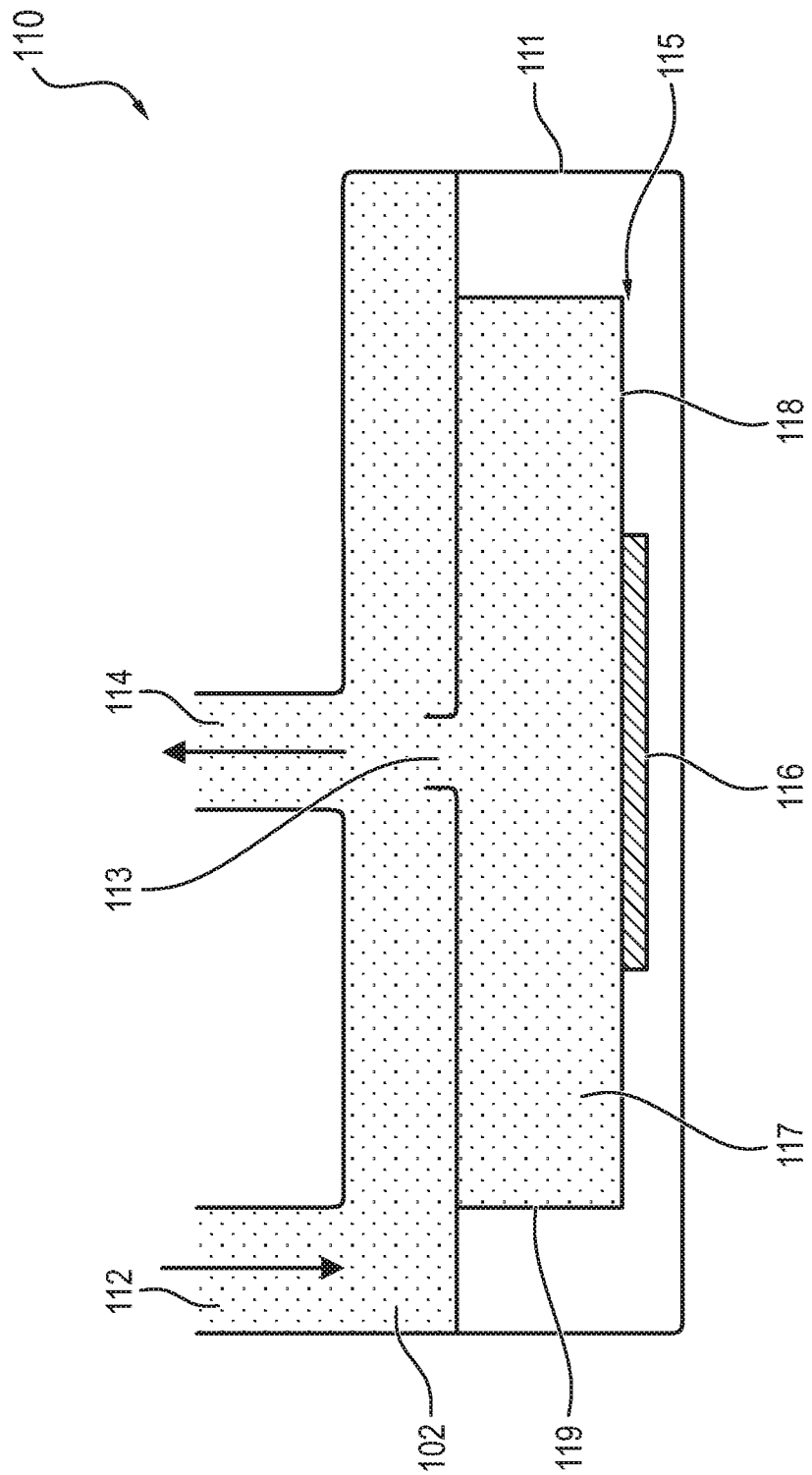
FIG. 6 is a schematic view of a micropump for use in a micropump system according to the present invention.

FIG. 6 shows a schematic view of a micropump 110 for use in a micropump system according to the present invention.

The micropump 110 has an outer housing 111 which forms a single intake opening 112 and a single outlet opening 114. In an exemplary embodiment, not shown, the micropump has a plurality of intake openings.

In the exemplary embodiment shown, the two openings 112, 114 are arranged on a top side of the housing. In an exemplary embodiment, not shown, one or both openings is/are arranged on a side of the housing different from the top side. A flow guide, which carries the drawn-in fluid 102 in a central area of the micropump 110, is located within the housing. A piezoelectric element 116 is arranged in a diaphragm 118 in order to make possible an electrical actuation of a vibration of the diaphragm 118 via a bending of the piezoelectric element 116. The diaphragm 118 and the piezoelectric element 116 form the inertia swing unit 115. The inertia swing unit 115 is arranged at a corresponding suspension 119. The electrical actuation of the inertia swing unit 115 is embodied by an electrical connection (not shown) of the piezoelectric element 116 to the printed circuit board.

Due to the architecture shown, the fluid 102 flowing through is pressed through the outlet opening. In this case, especially a guide opening 113 of a chamber 117 defined by the diaphragm 118 leads to a directed transport of the fluid 102 from the intake opening 112 to the outlet opening 114 because of the movement of the diaphragm 118.

Other possible architectures of micropumps are known to the person skilled in the art. In particular, the micropump system according to the present invention is not limited to a concrete configuration of the micropump and/or of the inertia swing unit. In an exemplary embodiment, not shown, the direction of the flow path is predefined by a nonreturn valve within the micropump system and/or the micropump.

Figure 7:
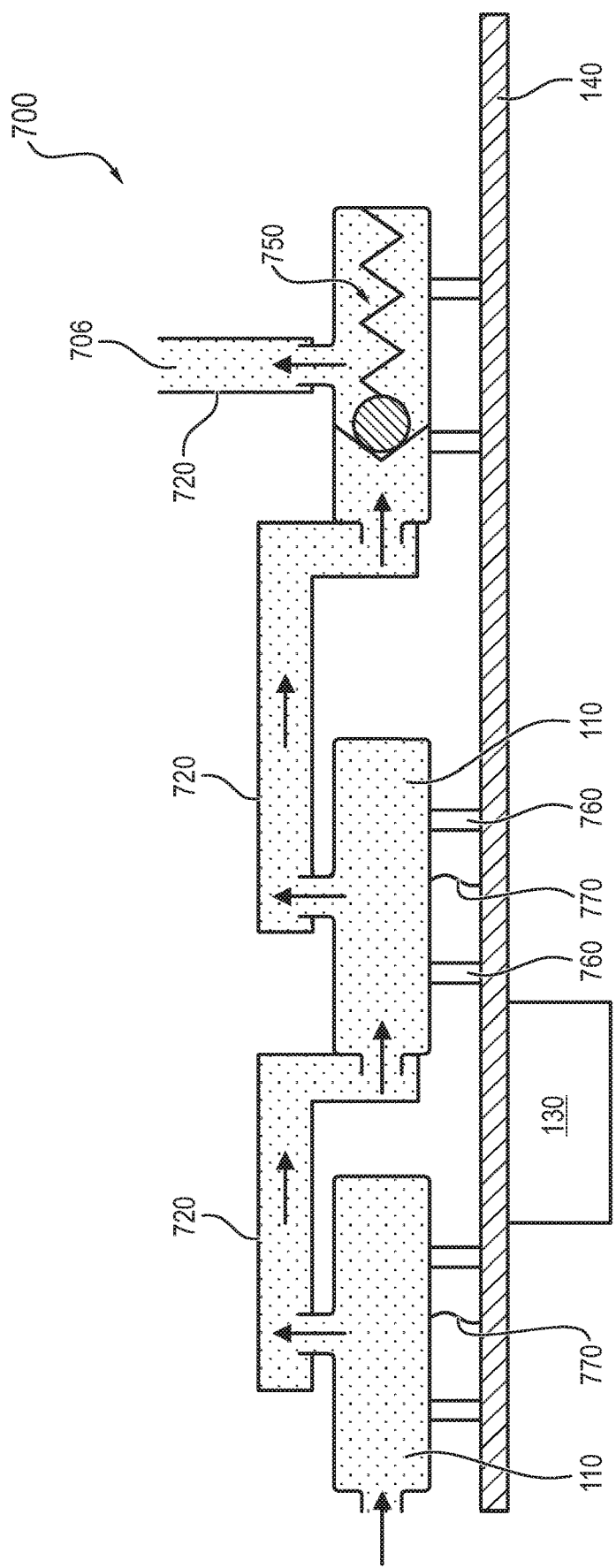
FIG. 7 is a schematic view of a fifth exemplary embodiment of a micropump system according to the present invention, in which a nonreturn valve is arranged in the area of a system outlet.

FIG. 7 shows a schematic view of a fifth exemplary embodiment of a micropump system 700 according to the present invention, in which a nonreturn valve 750 is arranged in the area of the system outlet 706.

The nonreturn valve 750 ensures that a minimum pressure is provided as the overall pump pressure by the micropump system 700. In an exemplary embodiment, not shown, such a minimum pressure is ensured by a pressure sensor within the micropump system, especially in the area of the system outlet.

Unlike in the previous exemplary embodiments, the two micropumps 110 in the micropump system 700 shown are fastened to the printed circuit board 140 via a plug-type connection 760. In an exemplary embodiment, not shown, the micropump is fastened to the printed circuit board by a soldering pad.

Furthermore, the number of flow duct elements 720 in the exemplary embodiment shown comprise three different flow duct elements 720, which each make possible a rigid connection to the micropumps connected thereto.

The respective electrical connection between the printed circuit board 140 and the micropump 110 is embodied via a separate electrical supply cable 770 in the exemplary embodiment shown. In an exemplary embodiment, not shown, the electrical connection is carried out via a plug-type connection between the micropump and the printed circuit board.

The control unit 130 can be configured at different positions on the printed circuit board or at a spaced location from the printed circuit board.

In all exemplary embodiments shown, each of the micropumps 110 comprising the plurality of micropumps is fastened to the flat printed circuit board 140 with the respective rigid fastening device such that all micropumps are arranged in a common fastening plane on the printed circuit board. Two such fastening planes are present only in the exemplary embodiment with two printed circuit boards shown in FIG. 5. The fastening plane is in this case preferably parallel to the plane formed by the printed circuit board 140.

The exemplary embodiments with a single printed circuit board represent especially preferred exemplary embodiments, since an especially simple and compact structure of the micropump system is possible due to a single printed circuit board.

In an exemplary embodiment, not shown, the micropumps within the micropump system are arranged in at least two different fastening planes, which are preferably both arranged parallel to a common printed circuit board for controlling these micropumps.

Figure 8:
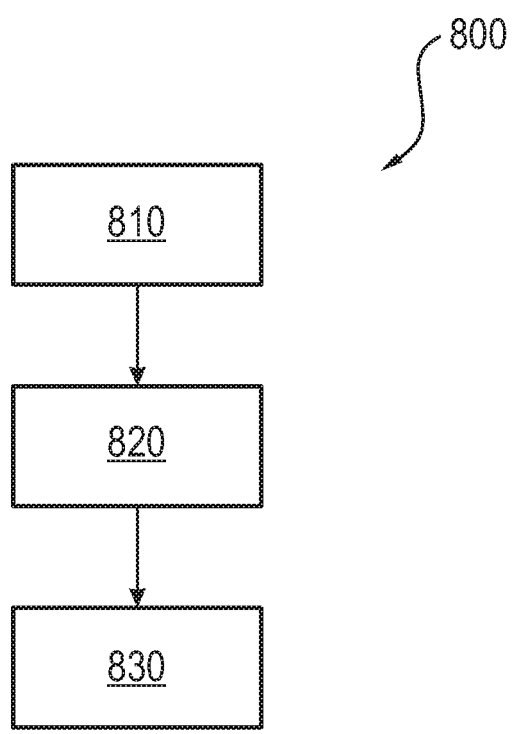
FIG. 8 is a flow chart of a process according to another aspect of the present invention.

FIG. 8 shows a flow chart of a process 800 according to another aspect of the present invention.

The process 800 according to the present invention for transport of a compressible fluid has in this case the steps described below.

A first step 810 comprises the provision of a plurality of micropumps, which have each an intake opening and an outlet opening for the fluid and which are each configured to draw in the fluid through the intake opening, which fluid flows through the correspondingly formed micropump system during the use thereof, due to an electrically controlled inertia swing unit of the respective micropump and to discharge same through the outlet opening.

A further step 820 comprises the formation of a flow path for the fluid due to a connection of a number of rigid flow duct elements to a respective micropump via a respective, elastically sealed port.

A next step 830 comprises the electrical connection of one or two printed circuit boards to the plurality of micropumps and the rigid fastening of each micropump from the plurality of micropumps via a respective fastening device to the one or two printed circuit boards. In this case, a pressure build-up of the fluid flowing through the plurality of micropumps during the use, which pressure build-up is cascaded due to plurality of micropumps, is provided at a system outlet of the micropump system.

The three steps 810, 820, 830 of this process are all carried out once during the manufacture of the micropump system. The operation of the micropump system includes the operation of the respective micropump, the alternating drawing in and discharge of which are already known.

The cascaded pressure build-up made possible by the process 800 due to the plurality of micropumps allows both a setting of an outputted overall pump pressure via a number of micropumps connected in series and a setting of an outputted overall flow of the fluid via a number of micropumps connected in parallel.

The process preferably comprises, furthermore, the formation of a common fastening plane on the printed circuit board, in which all micropumps are fastened via the rigid fastening device. This fastening plane is advantageously arranged parallel to the flat printed circuit board.

While specific embodiments of the invention have been shown and described in detail to illustrate the application of the principles of the invention, it will be understood that the invention may be embodied otherwise without departing from such principles.

LIST OF REFERENCE NUMBERS 100, 200, 400, 500, 700 Micropump system
102 Fluid
104 Flow path
106, 206, 406, 506, 706 System outlet
108, 208, 408, 408' System inlet
110 Micropump
111 Housing
112, 212 Intake opening
113 Guide opening
114, 214 Outlet opening
115 Inertia swing unit
116 Piezoelectric element
117 Chamber
118 Diaphragm
119 Suspension
120, 220, 420, 520, 720 Flow duct element
122 Port
124 Blocking element
130 Control unit
140, 140' Printed circuit board
142 Soldered joint
226 Feed line
228 Discharge line
432 Cable
750 Nonreturn valve
760 Plug-type connection
770 Supply cable
800 Process
810, 820, 830 Process steps

What is claimed is:

1. A micropump system for transporting a compressible fluid, the micropump system comprising:
   a plurality of micropumps, each of the plurality of micropumps comprising an electrically controlled inertia swing unit and having an intake opening and an outlet opening for the fluid and each of the plurality of micropumps being configured, with operation of the electrically controlled inertia swing unit, to draw in the fluid through the intake opening and discharge the fluid through the outlet opening, whereby fluid flows through the micropump system during use thereof;
   a number of rigid flow duct elements, each of the number of rigid flow duct elements being connected via an elastically sealed port to the intake opening and to the outlet opening of each one of the plurality of micropumps, the number of rigid flow duct elements comprising a plurality of blocking elements, wherein each of the plurality of blocking elements is arranged in an area of a corresponding micropump of the plurality of micropumps such that the fluid is carried through the corresponding micropump, wherein the number of rigid flow duct elements together with the plurality of blocking elements and the plurality of micropumps form a flow path for the fluid;
   a control unit configured to control operation of the plurality of micropumps;
   one or two printed circuit boards arranged and configured to electrically connect the control unit to the plurality of micropumps; and
   fastening devices, wherein each of the plurality of micropumps is rigidly fastened to the one or two printed circuit boards via one of the fastening devices, and wherein during use of the micropump system a pressure build-up of the fluid flowing through the plurality of micropumps is cascaded, due to the plurality of micropumps, and provided at a system outlet of the micropump system.

2. The micropump system in accordance with claim 1, wherein at least one of the rigid flow duct elements rigidly connects a respective outlet opening of one of the micropumps, which is arranged upstream in relation to a direction of flow of the fluid flowing through the micropump system, to a respective intake opening of one of the micropumps, which is arranged downstream in relation to the direction of flow.

3. The micropump system in accordance with claim 2, wherein each of the plurality of micropumps is connected to another of the plurality of micropumps by the rigid flow duct elements with the outlet opening of a respective upstream micropump connected to an intake opening of a respective downstream micropump.

4. The micropump system in accordance with claim 1, wherein:
   the number of the rigid flow duct elements are configured and arranged to form a feed line and a discharge line;
   the feed line is rigidly connected to all intake openings of the plurality of micropumps; and
   the discharge line is rigidly connected to all outlet openings of the plurality of micropumps.

5. The micropump system in accordance with claim 1, wherein the respective, elastically sealed port is elastically sealed via an O-ring.

6. The micropump system in accordance with claim 1, wherein each fastening device is formed by a soldering pad, a soldering pin or a plug connection.

7. The micropump system in accordance with claim 1, further comprising a nonreturn valve arranged at the system outlet of the micropump system for ensuring a minimum pressure provided by the micropump system.

8. The micropump system in accordance with claim 1, wherein:
the one or two printed circuit boards comprises a flat printed circuit board on which the plurality of micropumps are fastened with a respective rigid fastening device such that each of the plurality of micropumps is arranged in a common fastening plane on the flat printed circuit board; and
the fastening plane is parallel to a plane formed by the flat printed circuit board.

9. The micropump system in accordance with claim 1, wherein the number of the rigid flow duct elements are connected to the micropumps such that the rigid flow duct elements form a common connection plane.

10. The micropump system in accordance with claim 9, wherein:
the one or two printed circuit boards comprises a flat printed circuit board on which the plurality of micropumps are fastened with one of the fastening devices such that each of the plurality of micropumps is arranged in a common fastening plane on the flat printed circuit board;
the common fastening plane is parallel to a plane formed by the flat printed circuit board; and
the connection plane is, furthermore, parallel to the plane formed by the printed circuit board.

11. The micropump system in accordance with claim 1, wherein an electrical connection between the printed circuit board and the respective micropump is formed by a soldered joint, an electrical cable and/or a plug connection.

12. The micropump system in accordance with claim 1, wherein:
the one or two printed circuit boards comprises two printed circuit boards aligned parallel to one another with two opposite sides; and
each of the plurality of micropumps is fastened to one of the two opposite sides between the two printed circuit boards.

13. The micropump system in accordance with claim 1, wherein the electrically controlled inertia swing unit comprises a diaphragm and a piezoelectric element in contact with the diaphragm.

14. The micropump system in accordance with claim 13, wherein the diaphragm comprises a chamber having a guide opening.

15. The micropump system in accordance with claim 14, wherein the diaphragm is configured to move based on actuation of the piezoelectric element such that the fluid in a respective one of the micropumps is pressed through the outlet opening.

16. The micropump system in accordance with claim 1, wherein each of the plurality of rigid flow duct elements extends parallel to a longitudinal axis of the one or two printed circuit boards, each of the blocking elements being arranged between the intake opening and the outlet opening of a respective one of the micropumps.

17. The micropump system in accordance with claim 1, wherein at least one of the rigid flow duct elements is located at a position above at least one of the micropumps, at least one of the blocking elements being arranged between the intake opening and the outlet opening of the at least one of the micropumps.

18. The micropump system in accordance with claim 1, wherein at least one of the micropumps is located between at least one of the rigid flow duct elements and one of the one or more two printed circuit boards.

19. The micropump system in accordance with claim 1, wherein each of the micropumps is mechanically and electrically fixed to one of the one or more two printed circuit boards via a soldered connection.

20. A process for transporting a compressible fluid, the process comprising the steps of:
providing a plurality of micropumps, which each have an intake opening and an outlet opening for the fluid and which are each configured to draw in the fluid through the intake opening, which fluid flows through a correspondingly formed micropump system during the use thereof, due to an electrically controlled inertia swing unit of the respective micropump and to discharge same through the outlet opening;
forming a flow path for the fluid due to a connection of a number of rigid flow duct elements to a respective micropump via a respective, elastically sealed port, the number of rigid flow duct elements comprising a plurality of blocking elements, wherein each of the plurality of blocking elements is arranged in an area of a corresponding micropump of the plurality of micropumps such that the fluid is carried through the corresponding micropump; and
providing an electrical connection of one or two printed circuit boards to the plurality of micropumps and rigidly fastening each of the plurality of micropumps, via a respective fastening device, to the one or two printed circuit boards, wherein a pressure build-up of the fluid flowing through the plurality of micropumps during the use, which pressure build-up is cascaded due to plurality of micropumps, is provided at a system outlet of the micropump system.

* * * * *